United States Patent
Colli et al.

(10) Patent No.: US 12,409,034 B2
(45) Date of Patent: Sep. 9, 2025

(54) ANNULOPLASTY RING WITH POSTERIOR LEAFLET FOR MINIMALLY INVASIVE TREATMENT

(71) Applicant: VALCARE MEDICAL, INC., Wilmington, DE (US)

(72) Inventors: Andrea Colli, Padua (IT); Nadav Yellin, Aven Yehuda (IL); Samuel Shaolian, Newport Beach, CA (US); Shuki Porath, Haifa (IL); Guy Shimel, Tel Aviv (IL)

(73) Assignee: Valcare Medical, Inc., Wilmington, DE (US)

(*) Notice: Subject to any disclaimer, the term of this patent is extended or adjusted under 35 U.S.C. 154(b) by 895 days.

(21) Appl. No.: 17/595,916

(22) PCT Filed: Jun. 11, 2020

(86) PCT No.: PCT/US2020/037294
§ 371 (c)(1),
(2) Date: Nov. 29, 2021

(87) PCT Pub. No.: WO2020/252200
PCT Pub. Date: Dec. 17, 2020

(65) Prior Publication Data
US 2022/0226116 A1    Jul. 21, 2022

Related U.S. Application Data

(60) Provisional application No. 62/859,975, filed on Jun. 11, 2019.

(51) Int. Cl.
*A61F 2/24* (2006.01)
(52) U.S. Cl.
CPC .......... *A61F 2/2448* (2013.01); *A61F 2/2463* (2013.01); *A61F 2/2466* (2013.01);
(Continued)

(58) Field of Classification Search
CPC .... A61F 2/2448; A61F 2/2463; A61F 2/2466; A61F 2210/0014; A61F 2220/0016; A61F 2/2409; A61F 2/2412
See application file for complete search history.

(56) References Cited

U.S. PATENT DOCUMENTS

| 4,602,911 A | 7/1986 | Ahmadi et al. |
| 4,874,378 A | 10/1989 | Hillstead |

(Continued)

FOREIGN PATENT DOCUMENTS

| CN | 2114422 U | 9/1992 |
| CN | 2633218 Y | 8/2004 |

(Continued)

OTHER PUBLICATIONS

PCT/US2020/037294, International Search Report and Written Opinion, Aug. 28, 2020, 7 pages.
(Continued)

*Primary Examiner* — Suba Ganesan
(74) *Attorney, Agent, or Firm* — Greenberg Traurig, LLP; Christopher C. Bolten; Robert D. Ward

(57) ABSTRACT

An annuloplasty ring is disclosed. The annuloplasty ring includes an outer tube, a plurality of anchors, and at least one synthetic leaflet. The synthetic leaflets are in mechanical communication with the annuloplasty ring at a plurality of points. The outer tube includes a plurality of windows. The plurality of anchors are positioned inside the outer tube and about a perimeter of the outer tube. The plurality of anchors are configured to be emitted from the plurality of windows in order to anchor the annuloplasty ring to a heart valve of a patient.

19 Claims, 17 Drawing Sheets

(52) U.S. Cl.
CPC ............. *A61F 2210/0014* (2013.01); *A61F 2220/0016* (2013.01); *A61F 2220/0033* (2013.01)

(56) References Cited

U.S. PATENT DOCUMENTS

| | | | |
|---|---|---|---|
| 4,953,540 A | 9/1990 | Ray et al. | |
| 5,080,662 A | 1/1992 | Paul | |
| 5,236,440 A | 8/1993 | Hlavacek | |
| 5,306,296 A | 4/1994 | Wright et al. | |
| 5,609,565 A | 3/1997 | Nakamura | |
| 5,695,518 A | 12/1997 | Laerum | |
| 5,716,370 A | 2/1998 | Williamson, IV et al. | |
| 5,855,614 A | 1/1999 | Stevens et al. | |
| 6,113,611 A | 9/2000 | Allen et al. | |
| 6,231,602 B1 | 5/2001 | Carpentier et al. | |
| 6,447,524 B1 | 9/2002 | Knodel et al. | |
| 6,619,291 B2 | 9/2003 | Hlavka et al. | |
| 6,629,534 B1 | 10/2003 | St. Goar et al. | |
| 6,669,687 B1 | 12/2003 | Saadat | |
| 6,689,048 B2 | 2/2004 | Vanden Hoek et al. | |
| 6,726,704 B1 | 4/2004 | Loshakove et al. | |
| 6,776,784 B2 | 8/2004 | Ginn | |
| 6,790,229 B1 | 9/2004 | Berreklouw | |
| 6,797,002 B2 | 9/2004 | Spence et al. | |
| 6,805,711 B2 | 10/2004 | Quijano et al. | |
| 6,869,444 B2 * | 3/2005 | Gabbay ................. | A61F 2/2466 |
| | | | 128/898 |
| 6,893,459 B1 | 5/2005 | Macoviak | |
| 7,101,395 B2 | 9/2006 | Tremulis et al. | |
| 7,114,953 B1 | 10/2006 | Wagner | |
| 7,175,660 B2 | 2/2007 | Cartledge et al. | |
| 7,238,191 B2 | 7/2007 | Bachmann | |
| 7,285,087 B2 | 10/2007 | Moaddeb et al. | |
| 7,297,150 B2 | 11/2007 | Cartledge et al. | |
| 7,569,072 B2 | 8/2009 | Berg et al. | |
| 7,594,887 B2 | 9/2009 | Moaddeb et al. | |
| 7,635,329 B2 | 12/2009 | Goldfarb et al. | |
| 7,655,040 B2 | 2/2010 | Douk et al. | |
| 7,717,954 B2 | 5/2010 | Solem et al. | |
| 7,722,668 B2 | 5/2010 | Moaddeb et al. | |
| 7,758,637 B2 | 7/2010 | Starksen et al. | |
| 7,828,819 B2 | 11/2010 | Webler et al. | |
| 7,837,729 B2 | 11/2010 | Gordon et al. | |
| 7,988,725 B2 | 8/2011 | Gross et al. | |
| 8,163,014 B2 | 4/2012 | Lane et al. | |
| 8,182,529 B2 | 5/2012 | Gordon et al. | |
| 8,236,049 B2 | 8/2012 | Rowe et al. | |
| 8,287,591 B2 | 10/2012 | Keidar et al. | |
| 8,518,107 B2 | 8/2013 | Tsukashima et al. | |
| 8,579,968 B1 | 11/2013 | Shannon et al. | |
| 8,690,939 B2 | 4/2014 | Miller et al. | |
| 8,821,570 B2 | 9/2014 | DuMontelle et al. | |
| 9,180,008 B2 | 11/2015 | Yellin et al. | |
| 9,402,721 B2 | 8/2016 | Buchbinder et al. | |
| 9,433,503 B2 | 9/2016 | Tsukashima et al. | |
| 9,839,519 B2 | 12/2017 | Shaolian et al. | |
| 9,877,833 B1 | 1/2018 | Bishop et al. | |
| 10,405,979 B2 | 9/2019 | Schaffner et al. | |
| 10,543,087 B2 | 1/2020 | Yellin et al. | |
| 10,779,945 B2 | 9/2020 | Buchbinder et al. | |
| 11,058,417 B2 | 7/2021 | Foerster et al. | |
| 11,191,536 B2 | 12/2021 | Foerster et al. | |
| 11,224,422 B2 | 1/2022 | Foerster et al. | |
| 11,298,230 B2 | 4/2022 | Shaolian et al. | |
| 11,382,749 B2 | 7/2022 | Yellin et al. | |
| 11,510,835 B2 | 11/2022 | Yellin et al. | |
| 11,534,300 B2 | 12/2022 | Yellin et al. | |
| 11,571,301 B2 | 2/2023 | Yellin et al. | |
| 11,571,307 B2 | 2/2023 | Yellin et al. | |
| 11,576,779 B2 | 2/2023 | Yellin et al. | |
| 11,617,647 B2 | 4/2023 | Yellin | |
| 11,654,018 B2 | 5/2023 | Shaolian et al. | |
| 11,793,628 B2 | 10/2023 | Dumontelle et al. | |
| 11,806,009 B2 | 11/2023 | Foerster et al. | |
| 11,806,237 B2 | 11/2023 | Rozen et al. | |
| 11,813,164 B2 | 11/2023 | Yellin et al. | |
| 11,857,418 B2 | 1/2024 | Yellin et al. | |
| 12,115,069 B2 | 10/2024 | Shaolian et al. | |
| 12,127,941 B2 | 10/2024 | Yellin et al. | |
| 2002/0151961 A1 | 10/2002 | Lashinski et al. | |
| 2002/0151970 A1 | 10/2002 | Garrison et al. | |
| 2002/0188170 A1 | 12/2002 | Santamore et al. | |
| 2002/0198526 A1 | 12/2002 | Shaolian et al. | |
| 2003/0050649 A1 | 3/2003 | Brock et al. | |
| 2003/0050693 A1 | 3/2003 | Quijano et al. | |
| 2003/0078465 A1 | 4/2003 | Pai et al. | |
| 2003/0078671 A1 | 4/2003 | Lesniak et al. | |
| 2003/0191528 A1 | 10/2003 | Quijano et al. | |
| 2003/0198605 A1 | 10/2003 | Montgomery | |
| 2003/0199974 A1 | 10/2003 | Lee et al. | |
| 2004/0044364 A1 | 3/2004 | DeVries et al. | |
| 2004/0068276 A1 | 4/2004 | Golden et al. | |
| 2004/0073237 A1 | 4/2004 | Leinsing | |
| 2004/0122514 A1 | 6/2004 | Fogarty et al. | |
| 2004/0138744 A1 | 7/2004 | Lashinski et al. | |
| 2004/0148021 A1 | 7/2004 | Cartledge et al. | |
| 2004/0193191 A1 | 9/2004 | Starksen et al. | |
| 2004/0243230 A1 | 12/2004 | Navia et al. | |
| 2004/0249391 A1 | 12/2004 | Cummins | |
| 2004/0260393 A1 | 12/2004 | Rahdert et al. | |
| 2004/0260394 A1 | 12/2004 | Douk et al. | |
| 2005/0004668 A1 | 1/2005 | Aklog et al. | |
| 2005/0020696 A1 | 1/2005 | Montgomery et al. | |
| 2005/0033325 A1 | 2/2005 | May et al. | |
| 2005/0065550 A1 | 3/2005 | Starksen et al. | |
| 2005/0090846 A1 | 4/2005 | Pedersen et al. | |
| 2005/0096740 A1 | 5/2005 | Langberg et al. | |
| 2005/0113910 A1 | 5/2005 | Paniagua et al. | |
| 2005/0137692 A1 | 6/2005 | Haug et al. | |
| 2005/0137695 A1 | 6/2005 | Salahieh et al. | |
| 2005/0203549 A1 | 9/2005 | Realyvasquez | |
| 2005/0222678 A1 | 10/2005 | Lashinski et al. | |
| 2005/0240200 A1 | 10/2005 | Bergheim | |
| 2005/0250161 A1 | 11/2005 | Suciu-Foca et al. | |
| 2005/0267572 A1 | 12/2005 | Schoon et al. | |
| 2005/0283190 A1 | 12/2005 | Huitema et al. | |
| 2005/0288778 A1 | 12/2005 | Shaoulian et al. | |
| 2005/0288781 A1 | 12/2005 | Moaddeb et al. | |
| 2006/0009737 A1 | 1/2006 | Whiting et al. | |
| 2006/0020327 A1 | 1/2006 | Lashinski et al. | |
| 2006/0020334 A1 * | 1/2006 | Lashinski ............. | A61F 2/2418 |
| | | | 623/2.11 |
| 2006/0052867 A1 | 3/2006 | Revuelta et al. | |
| 2006/0122633 A1 | 6/2006 | To et al. | |
| 2006/0129025 A1 | 6/2006 | Levine et al. | |
| 2006/0155165 A1 | 7/2006 | Vanden Hoek et al. | |
| 2006/0161169 A1 | 7/2006 | Nieminen et al. | |
| 2006/0184240 A1 | 8/2006 | Jimenez et al. | |
| 2006/0184242 A1 | 8/2006 | Lichtenstein | |
| 2006/0195134 A1 | 8/2006 | Crittenden | |
| 2006/0195183 A1 | 8/2006 | Navia et al. | |
| 2006/0241748 A1 | 10/2006 | Lee et al. | |
| 2006/0282161 A1 | 12/2006 | Huynh et al. | |
| 2007/0016287 A1 | 1/2007 | Cartledge et al. | |
| 2007/0027533 A1 | 2/2007 | Douk | |
| 2007/0038296 A1 | 2/2007 | Navia | |
| 2007/0051377 A1 | 3/2007 | Douk et al. | |
| 2007/0067027 A1 | 3/2007 | Moaddeb et al. | |
| 2007/0073098 A1 | 3/2007 | Lenker et al. | |
| 2007/0080188 A1 | 4/2007 | Spence et al. | |
| 2007/0093854 A1 | 4/2007 | Kayan | |
| 2007/0118215 A1 | 5/2007 | Moaddeb | |
| 2007/0128132 A1 | 6/2007 | Piergallini et al. | |
| 2007/0135913 A1 | 6/2007 | Moaddeb et al. | |
| 2007/0142907 A1 | 6/2007 | Moaddeb et al. | |
| 2007/0213812 A1 | 9/2007 | Webler et al. | |
| 2007/0233239 A1 | 10/2007 | Navia et al. | |
| 2007/0239272 A1 | 10/2007 | Navia et al. | |
| 2007/0244553 A1 | 10/2007 | Rafiee et al. | |
| 2007/0244554 A1 | 10/2007 | Rafiee et al. | |
| 2007/0244555 A1 | 10/2007 | Rafiee et al. | |
| 2007/0244556 A1 | 10/2007 | Rafiee et al. | |
| 2007/0250161 A1 | 10/2007 | Dolan | |

(56) References Cited

U.S. PATENT DOCUMENTS

| | | |
|---|---|---|
| 2007/0293942 A1 | 12/2007 | Mirzaee |
| 2008/0039934 A1 | 2/2008 | Styrc |
| 2008/0051807 A1 | 2/2008 | St Goar et al. |
| 2008/0065011 A1 | 3/2008 | Marchand et al. |
| 2008/0177380 A1 | 7/2008 | Starksen et al. |
| 2008/0177381 A1 | 7/2008 | Navia et al. |
| 2008/0200980 A1 | 8/2008 | Robin et al. |
| 2008/0208327 A1 | 8/2008 | Rowe |
| 2008/0215145 A1 | 9/2008 | Moaddeb et al. |
| 2008/0243220 A1 | 10/2008 | Barker |
| 2008/0262513 A1 | 10/2008 | Stahler et al. |
| 2008/0262609 A1 | 10/2008 | Gross et al. |
| 2008/0288060 A1 | 11/2008 | Kaye et al. |
| 2008/0306586 A1 | 12/2008 | Cartledge et al. |
| 2009/0076599 A1 | 3/2009 | Bergin |
| 2009/0088838 A1 | 4/2009 | Shaolian et al. |
| 2009/0118747 A1 | 5/2009 | Bettuchi et al. |
| 2009/0125098 A1 | 5/2009 | Chuter |
| 2009/0149872 A1 | 6/2009 | Gross et al. |
| 2009/0216322 A1 | 8/2009 | Le et al. |
| 2009/0222083 A1 | 9/2009 | Nguyen et al. |
| 2009/0238778 A1 | 9/2009 | Mordas et al. |
| 2009/0299470 A1 | 12/2009 | Rao et al. |
| 2010/0010616 A1 | 1/2010 | Drews et al. |
| 2010/0030014 A1 | 2/2010 | Ferrazzi |
| 2010/0063586 A1 | 3/2010 | Hasenkam et al. |
| 2010/0076549 A1 | 3/2010 | Keidar et al. |
| 2010/0121433 A1 | 5/2010 | Bolling et al. |
| 2010/0161047 A1 | 6/2010 | Cabiri |
| 2010/0185274 A1 | 7/2010 | Moaddeb et al. |
| 2010/0191327 A1 | 7/2010 | Lane et al. |
| 2010/0204713 A1 | 8/2010 | Ruiz Morales |
| 2010/0211166 A1 | 8/2010 | Miller et al. |
| 2010/0249920 A1 | 9/2010 | Bolling et al. |
| 2010/0262232 A1 | 10/2010 | Annest |
| 2010/0266989 A1 | 10/2010 | Piergallini et al. |
| 2010/0280604 A1 | 11/2010 | Zipory et al. |
| 2010/0280605 A1 | 11/2010 | Hammer et al. |
| 2010/0286767 A1 | 11/2010 | Zipory et al. |
| 2011/0004299 A1 | 1/2011 | Navia et al. |
| 2011/0011917 A1 | 1/2011 | Loulmet |
| 2011/0022168 A1 | 1/2011 | Cartledge |
| 2011/0027753 A1 | 2/2011 | Maurat et al. |
| 2011/0034953 A1 | 2/2011 | Milo |
| 2011/0034999 A1 | 2/2011 | Carpentier et al. |
| 2011/0060407 A1 | 3/2011 | Ketai et al. |
| 2011/0066231 A1 | 3/2011 | Cartledge et al. |
| 2011/0093062 A1 | 4/2011 | Cartledge et al. |
| 2011/0106245 A1 | 5/2011 | Miller et al. |
| 2011/0106247 A1 | 5/2011 | Miller et al. |
| 2011/0137397 A1 | 6/2011 | Chau et al. |
| 2011/0166649 A1 | 7/2011 | Gross et al. |
| 2011/0190879 A1 | 8/2011 | Bobo et al. |
| 2011/0208295 A1 | 8/2011 | Cartledge et al. |
| 2011/0208298 A1 | 8/2011 | Tuval et al. |
| 2011/0224785 A1 | 9/2011 | Hacohen |
| 2011/0257728 A1 | 10/2011 | Kuehn |
| 2011/0282361 A1 | 11/2011 | Miller et al. |
| 2011/0301698 A1 | 12/2011 | Miller et al. |
| 2011/0301699 A1 | 12/2011 | Saadat |
| 2011/0319989 A1 | 12/2011 | Lane et al. |
| 2012/0022557 A1 | 1/2012 | Cabiri et al. |
| 2012/0022639 A1 | 1/2012 | Hacohen et al. |
| 2012/0022644 A1 | 1/2012 | Reich et al. |
| 2012/0059458 A1 | 3/2012 | Buchbinder et al. |
| 2012/0083880 A1 | 4/2012 | Rankin et al. |
| 2012/0095455 A1 | 4/2012 | Rodmond et al. |
| 2012/0123531 A1* | 5/2012 | Tsukashima .......... A61F 2/2448 623/2.37 |
| 2012/0136436 A1 | 5/2012 | Cabiri et al. |
| 2012/0136463 A1 | 5/2012 | Muniz |
| 2012/0165930 A1 | 6/2012 | Gifford, III et al. |
| 2012/0245604 A1 | 9/2012 | Tegzes |
| 2012/0310330 A1 | 12/2012 | Buchbinder et al. |
| 2013/0066342 A1 | 3/2013 | Dell et al. |
| 2013/0087598 A1 | 4/2013 | Surti |
| 2013/0116780 A1 | 5/2013 | Miller et al. |
| 2013/0166022 A1 | 6/2013 | Conklin |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0282114 A1 | 10/2013 | Schweich, Jr. et al. |
| 2013/0289718 A1 | 10/2013 | Tsukashima et al. |
| 2013/0289720 A1 | 10/2013 | Dobrilovic |
| 2013/0304197 A1 | 11/2013 | Buchbinder et al. |
| 2014/0005778 A1 | 1/2014 | Buchbinder et al. |
| 2014/0025163 A1 | 1/2014 | Padalla et al. |
| 2014/0046433 A1 | 2/2014 | Kovalsky |
| 2014/0058505 A1 | 2/2014 | Bielefeld |
| 2014/0114407 A1 | 4/2014 | Rajamannan |
| 2014/0188130 A1 | 7/2014 | Sanchez et al. |
| 2014/0214157 A1 | 7/2014 | Börtlein et al. |
| 2014/0277411 A1 | 9/2014 | Börtlein et al. |
| 2014/0364939 A1 | 12/2014 | Deshmukh et al. |
| 2015/0073420 A1 | 3/2015 | Bookwalter et al. |
| 2015/0112432 A1 | 4/2015 | Reich et al. |
| 2015/0127093 A1 | 5/2015 | Hosmer et al. |
| 2015/0173897 A1 | 6/2015 | Raanani et al. |
| 2015/0173987 A1 | 6/2015 | Albinmousa et al. |
| 2015/0351903 A1 | 12/2015 | Morriss et al. |
| 2015/0366666 A1 | 12/2015 | Khairkhahan et al. |
| 2016/0022419 A1 | 1/2016 | Yellin et al. |
| 2016/0038286 A1 | 2/2016 | Yellin et al. |
| 2016/0089235 A1 | 3/2016 | Yellin |
| 2016/0100897 A1 | 4/2016 | Avalos et al. |
| 2016/0106420 A1 | 4/2016 | Foerster et al. |
| 2016/0120642 A1 | 5/2016 | Shaolian et al. |
| 2016/0120645 A1 | 5/2016 | Alon |
| 2016/0220371 A1 | 8/2016 | Keane |
| 2016/0270911 A1 | 9/2016 | Ganesan et al. |
| 2016/0331534 A1 | 11/2016 | Buchbinder et al. |
| 2017/0042670 A1 | 2/2017 | Shaolian et al. |
| 2017/0231763 A1 | 8/2017 | Yellin |
| 2017/0258590 A1 | 9/2017 | Khairkhahan |
| 2017/0296340 A1 | 10/2017 | Gross et al. |
| 2017/0325948 A1 | 11/2017 | Wallace et al. |
| 2018/0028387 A1 | 2/2018 | Yellin et al. |
| 2018/0042723 A1 | 2/2018 | Yellin et al. |
| 2018/0098849 A1 | 4/2018 | Yellin et al. |
| 2018/0161160 A1 | 6/2018 | Shaolian et al. |
| 2018/0161161 A1 | 6/2018 | Yellin et al. |
| 2018/0228610 A1 | 8/2018 | Lashinski et al. |
| 2018/0235758 A1* | 8/2018 | Biadillah ................ A61F 2/246 |
| 2018/0325670 A1 | 11/2018 | De |
| 2019/0053905 A1 | 2/2019 | Alon |
| 2019/0083091 A1 | 3/2019 | Foerster et al. |
| 2019/0083092 A1 | 3/2019 | Foerster et al. |
| 2019/0083239 A1 | 3/2019 | Shaolian et al. |
| 2019/0083240 A1* | 3/2019 | Shaolian ................ A61F 2/2409 |
| 2019/0091022 A1 | 3/2019 | Yellin et al. |
| 2019/0133765 A1 | 5/2019 | Yellin et al. |
| 2020/0069426 A1 | 3/2020 | Conklin et al. |
| 2020/0163763 A1 | 5/2020 | Zipory et al. |
| 2020/0170799 A1 | 6/2020 | Yellin et al. |
| 2020/0330228 A1 | 10/2020 | Anderson et al. |
| 2021/0085463 A1 | 3/2021 | Yellin et al. |
| 2021/0161662 A1 | 6/2021 | Albes |
| 2021/0346159 A1* | 11/2021 | Keränen ................ A61F 2/2448 |
| 2021/0353417 A1 | 11/2021 | Yellin et al. |
| 2022/0226771 A1 | 7/2022 | Lipscomb |
| 2023/0040083 A1 | 2/2023 | Gifford, III et al. |
| 2023/0045532 A1 | 2/2023 | Galler et al. |
| 2023/0372086 A1 | 11/2023 | Galler et al. |

FOREIGN PATENT DOCUMENTS

| | | |
|---|---|---|
| CN | 101411632 A | 4/2009 |
| CN | 101460113 A | 6/2009 |
| CN | 101553190 A | 10/2009 |
| CN | 102014797 A | 4/2011 |
| CN | 102088930 A | 6/2011 |
| CN | 202859386 U | 4/2013 |
| CN | 103179920 A | 6/2013 |
| CN | 103237523 A | 8/2013 |

(56) References Cited

FOREIGN PATENT DOCUMENTS

| | | |
|---|---|---|
| CN | 103735337 A | 4/2014 |
| CN | 203954080 U | 11/2014 |
| CN | 108618871 A | 10/2018 |
| CN | 113855324 A | 12/2021 |
| DE | 102014102653 A1 | 9/2015 |
| EP | 1752115 A1 | 2/2007 |
| EP | 2471464 A1 | 7/2012 |
| EP | 2600799 A2 | 6/2013 |
| EP | 2928538 A1 | 10/2015 |
| EP | 2967700 A1 | 1/2016 |
| EP | 2600799 B1 | 5/2017 |
| EP | 3213715 A1 | 9/2017 |
| EP | 2928538 B1 | 11/2018 |
| FR | 2845889 A1 | 4/2004 |
| GB | 1496804 A | 1/1978 |
| GB | 2366319 A | 3/2002 |
| KR | 20040095482 A | 11/2004 |
| RU | 125062 U1 | 2/2013 |
| WO | WO-8000673 A1 | 4/1980 |
| WO | WO-9009153 A1 | 8/1990 |
| WO | WO-9728745 A1 | 8/1997 |
| WO | WO-03017874 A1 | 3/2003 |
| WO | WO-03047467 A1 | 6/2003 |
| WO | WO-2005046488 A2 | 5/2005 |
| WO | WO-2007035882 A2 | 3/2007 |
| WO | WO-2008097999 A2 | 8/2008 |
| WO | WO-2009052427 A1 | 4/2009 |
| WO | WO-2009120764 A2 | 10/2009 |
| WO | WO-2010004546 A1 | 1/2010 |
| WO | WO-2010085659 A1 | 7/2010 |
| WO | WO-2011011443 A2 | 1/2011 |
| WO | WO-2011097355 A2 | 8/2011 |
| WO | WO-2011154942 A2 | 12/2011 |
| WO | WO-2012004679 A2 | 1/2012 |
| WO | WO-2012019052 A2 | 2/2012 |
| WO | WO-2012038550 A1 | 3/2012 |
| WO | WO-2012040865 A1 | 4/2012 |
| WO | WO-2012063228 A1 | 5/2012 |
| WO | WO-2012095159 A2 | 7/2012 |
| WO | WO-2012106354 A1 | 8/2012 |
| WO | WO-2012167095 A2 | 12/2012 |
| WO | WO-2013095816 A1 | 6/2013 |
| WO | WO-2013128436 A1 | 9/2013 |
| WO | WO-2013130641 A1 | 9/2013 |
| WO | WO-2013175468 A2 | 11/2013 |
| WO | WO-2014089424 A1 | 6/2014 |
| WO | WO-2014145399 A1 | 9/2014 |
| WO | WO-2014178869 A1 | 11/2014 |
| WO | WO-2014189509 A1 | 11/2014 |
| WO | WO-2014190329 A1 | 11/2014 |
| WO | WO-2014210600 A2 | 12/2014 |
| WO | WO-2015052629 A1 | 4/2015 |
| WO | WO-2015132668 A1 | 9/2015 |
| WO | WO-2016025894 A1 | 2/2016 |
| WO | WO-2016040526 A1 | 3/2016 |
| WO | WO-2018035118 A1 | 2/2018 |
| WO | WO-2018071540 A1 | 4/2018 |
| WO | WO-2018170424 A1 | 9/2018 |
| WO | WO-2020117842 A1 | 6/2020 |
| WO | WO-2020252200 A1 | 12/2020 |

OTHER PUBLICATIONS

Extended European Search Report for European Application No. 11815347.7, mailed Mar. 14, 2016, 10 Pages.
Extended European Search Report for European Application No. 12793292.9, mailed Dec. 1, 2014, 6 Pages.
Extended European Search Report for European Application No. 13755441.6, mailed Mar. 1, 2016, 12 Pages.
Extended European Search Report for European Application No. 13860442.6, mailed Aug. 11, 2016, 7 pages.
Extended European Search Report for European Application No. 13885021.9, mailed Jan. 3, 2017, 8 Pages.
Extended European Search Report for European Application No. 14762806.9, mailed Jul. 29, 2016, 7 Pages.
Extended European Search Report for European Application No. 14801009.3, mailed Dec. 5, 2016, 8 Pages.
Extended European Search Report for European Application No. 14817662.1, mailed Jan. 23, 2017, 7 Pages.
Extended European Search Report for European Application No. 17155803.4, mailed Aug. 9, 2017, 10 Pages.
Extended European Search Report for European Application No. 17835256.3, mailed Feb. 12, 2020, 9 Pages.
Extended European Search Report for European Application No. 17841988.3, mailed Dec. 16, 2019, 8 Pages.
Extended European Search Report for European Application No. 17860901.2, mailed Jun. 5, 2020, 06 Pages.
Extended European Search Report for European Application No. 18768197.8, mailed Oct. 19, 2020, 7 Pages.
Extended European Search Report for European Application No. 19151726.7, mailed Jul. 22, 2019, 9 Pages.
Extended European Search Report for European Application No. 19170261.2, mailed Aug. 5, 2019, 9 pages.
Extended European Search Report for European Application No. 19893113.1, mailed Nov. 17, 2022, 7 Pages.
Extended European Search Report for European Application No. 20206790.6, mailed Dec. 7, 2020, 9 Pages.
Extended European Search Report for European Application No. 20209605.3, mailed Mar. 9, 2021, 7 pages.
Extended European Search Report for European Application No. 20823198.5, mailed May 15, 2023, 15 Pages.
Extended European Search Report for European Application No. 20823682.8, mailed Apr. 14, 2023, 10 Pages.
Extended European Search Report for European Application No. 20841346.8, mailed Jul. 21, 2023, 9 Pages.
International Search Report & Written Opinion dated Jul. 24, 2024 in Int'l PCT Patent Appl. Serial No. PCT/US2024/019797.
International Search Report and Written Opinion for International Application No. PCT/IL2022/050868, mailed Nov. 17, 2022, 19 Pages.
International Search Report and Written Opinion for International Application No. PCT/IL2023/050527, mailed Aug. 8, 2023, 14 Pages.
International Search Report and Written Opinion for International Application No. PCT/US2011/046659, mailed Jun. 4, 2012, 13 Pages.
International Search Report and Written Opinion for International Application No. PCT/US2012/040481, mailed Dec. 6, 2012, 12 Pages.
International Search Report and Written Opinion for International Application No. PCT/US2013/028065, mailed Jun. 27, 2013, 11 Pages.
International Search Report and Written Opinion for International Application No. PCT/US2013/042275, mailed Feb. 20, 2014, 18 Pages.
International Search Report and Written Opinion for International Application No. PCT/US2013/058102, mailed Apr. 21, 2014, 10 Pages.
International Search Report and Written Opinion for International Application No. PCT/US2013/073552, mailed Mar. 6, 2014, 10 Pages.
International Search Report and Written Opinion for International Application No. PCT/US2014/030163, mailed Aug. 27, 2014, 10 Pages.
International Search Report and Written Opinion for International Application No. PCT/US2014/039454, mailed Oct. 22, 2014, 11 Pages.
International Search Report and Written Opinion for International Application No. PCT/US2014/044920, mailed Dec. 24, 2014, 15 Pages.
International Search Report and Written Opinion for International Application No. PCT/US2017/044129, mailed Sep. 27, 2017, 9 Pages.
International Search Report and Written Opinion for International Application No. PCT/US2017/046933, mailed Dec. 21, 2017, 11 Pages.

(56) References Cited

OTHER PUBLICATIONS

International Search Report and Written Opinion for International Application No. PCT/US2017/056138, mailed Jan. 8, 2018, 6 Pages.
International Search Report and Written Opinion for International Application No. PCT/US2018/022910, mailed May 23, 2018, 7 Pages.
International Search Report and Written Opinion for International Application No. PCT/US2019/064289, mailed Feb. 5, 2020, 8 Pages.
International Search Report and Written Opinion for International Application No. PCT/US2020/037296, mailed Sep. 10, 2020, 8 Pages.
International Search Report and Written Opinion for International Application No. PCT/US2020/042201, mailed Oct. 9, 2020, 7 Pages.
International Search Report and Written Opinion for International Application No. PCT/US2021/071467, mailed Jan. 14, 2022, 12 Pages.
International Search Report and Written Opinion for International Application No. PCT/US2021/071468, mailed Jan. 19, 2022, 8 Pages.
Partial Supplementary European Search Report for European Application No. 11815347.7, mailed Nov. 16, 2015, 06 Pages.
Partial Supplementary European Search Report for European Application No. 13755441.6, mailed Nov. 3, 2015, 7 Pages.

\* cited by examiner

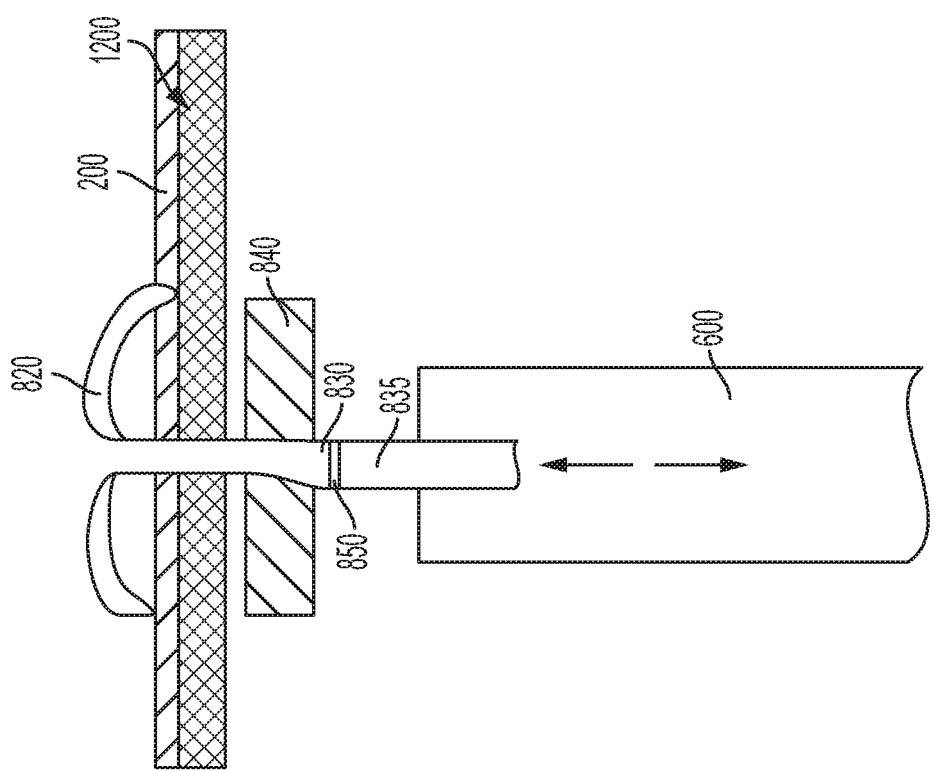

ANNULOPLASTY RING WITH POSTERIOR LEAFLET FOR MINIMALLY INVASIVE TREATMENT

CLAIM OF PRIORITY

The present application is a national stage filing under 35 U.S.C. § 371 of International Patent Application No. PCT/US2020/037294, filed Jun. 11, 2020, which claims priority under 35 U.S.C. § 119(e) to U.S. Provisional Patent Application No. 62/859,975, filed on Jun. 11, 2019, titled "ANNULOPLASTY RING WITH POSTERIOR LEAFLET FOR MINIMALLY INVASIVE TREATMENT," each of which is hereby incorporated by reference herein in its entirety.

TECHNICAL FIELD

The present disclosure relates to implantable prosthetic devices. More specifically, the disclosure is directed to an improved prosthetic device implantable by catheter for the treatment of mitral or tricuspid regurgitation.

BACKGROUND

Mitral regurgitation is a valvular dysfunction that causes blood volume to flow during systole (during left ventricular contraction) from the left ventricle to the left atrium as opposed to a healthy heart where this direction of flow is blocked by the mitral valve. The reverse flow during systole causes pressure to rise in the left atrium. Maintaining a normal cardiac output results in an increased left ventricle pressure.

Treating patients with mitral regurgitation (MR) or tricuspid regurgitation (TR) could require valve replacement in order to reduce or eliminate the regurgitation. For many years, the commonly accepted treatment was surgical repair or replacement of the native valve during open heart surgery. In recent years, a trans-vascular technique has been developed for introducing and implanting a prosthetic heart valve using a flexible catheter in a manner that is less invasive than open heart surgery.

In the trans-vascular technique, the prosthetic is delivered to the target site (aortic valve, mitral valve, tricuspid valve, or other valve) through a catheter while the device is crimped to a low diameter shaft, and expanded/deployed to the functional size when it is located in the correct position.

The catheter can be advanced to the target site: (a) Through the vascular system, where a catheter is advanced from the femoral vein/artery or any other blood vessel that allows access to the target site; (b) Trans-apically, where a catheter is advanced through a small incision made in the chest wall and then through the apex; or (c) Trans-atrially, where a catheter is advanced through a small incision made in the chest wall and then through the left or right atrium.

SUMMARY

Some embodiments disclosed herein are directed towards an annuloplasty ring for heart valve repair. In some embodiments, the annuloplasty ring may have a first end and a second end opposite the first end. The annuloplasty ring may be configured to have an elongate insertion geometry and an annular operable geometry. The annuloplasty ring may further comprise a plurality of anchors within the annuloplasty ring. The plurality of anchors may have a deployment configuration in the annular operable geometry. The annuloplasty ring may comprise at least one synthetic leaflet in mechanical communication with the annuloplasty ring at a plurality of points. In some embodiments, the at least one synthetic leaflet may comprise a valve frame having a proximal opening and a synthetic leaflet material mechanically coupled to the valve frame. The synthetic leaflet material may be located within the proximal opening. In some embodiments, the valve frame may comprise a shape memory metal. In further embodiments, the synthetic leaflet material may comprise a polymeric material.

In some embodiments, the at least one synthetic leaflet of the annuloplasty ring may comprise a plurality of leaflets. In further embodiments, the plurality of leaflets may have a first leaflet positioned adjacent to the first end of the annuloplasty ring and a second leaflet positioned adjacent to the second end of the annuloplasty ring. In some embodiments, at least a portion of the first leaflet and the second leaflet are mechanically coupled.

In some embodiments, the at least one synthetic leaflet is in mechanical communication with the annuloplasty ring at a plurality of points on a posterior side or an anterior side of a native valve.

In additional embodiments, the annuloplasty device may further comprise a plurality of anchor windows, a coating, a DACRON (i.e., polyethylene terephthalate) coating, a shape memory metal, or a combination thereof. In some embodiments, the at least one synthetic leaflet may comprise one or more lace holes. In further embodiments, the annuloplasty ring may further comprise at least one snap mechanism configured to connect the first end and the second end.

Further embodiments disclosed herein are directed towards an anchor device. The anchor device may comprise a leaflet anchor having an anchor body with a first end and a second end. The leaflet anchor may further comprise an anchor portion in mechanical communication with the first end of the leaflet anchor. In some embodiments, the leaflet anchor may further comprise a separating element in mechanical communication with the second end of the leaflet anchor, and a distal portion in mechanical communication with the anchor body between the first end and the second end. In some embodiments, the separating element may be configured to rotate the anchor body. In further embodiments, the anchor portion or the anchor body may comprise a shape memory metal.

Additional embodiments disclosed herein are directed towards a method of delivering the annuloplasty ring in an elongate insertion geometry, where the delivery of the annuloplasty ring utilizes one of a trans-apical approach, trans-septal approach, a trans-femoral approach, a trans-jugular approach, and a trans-atrial approach.

BRIEF DESCRIPTION OF THE DRAWINGS

Aspects, features, benefits and advantages of the embodiments described herein will be apparent with regard to the following description, appended claims, and accompanying drawings where:

FIG. 11B depicts a deployed leaflet anchor in accordance with an embodiment.

DETAILED DESCRIPTION

Figure 1:
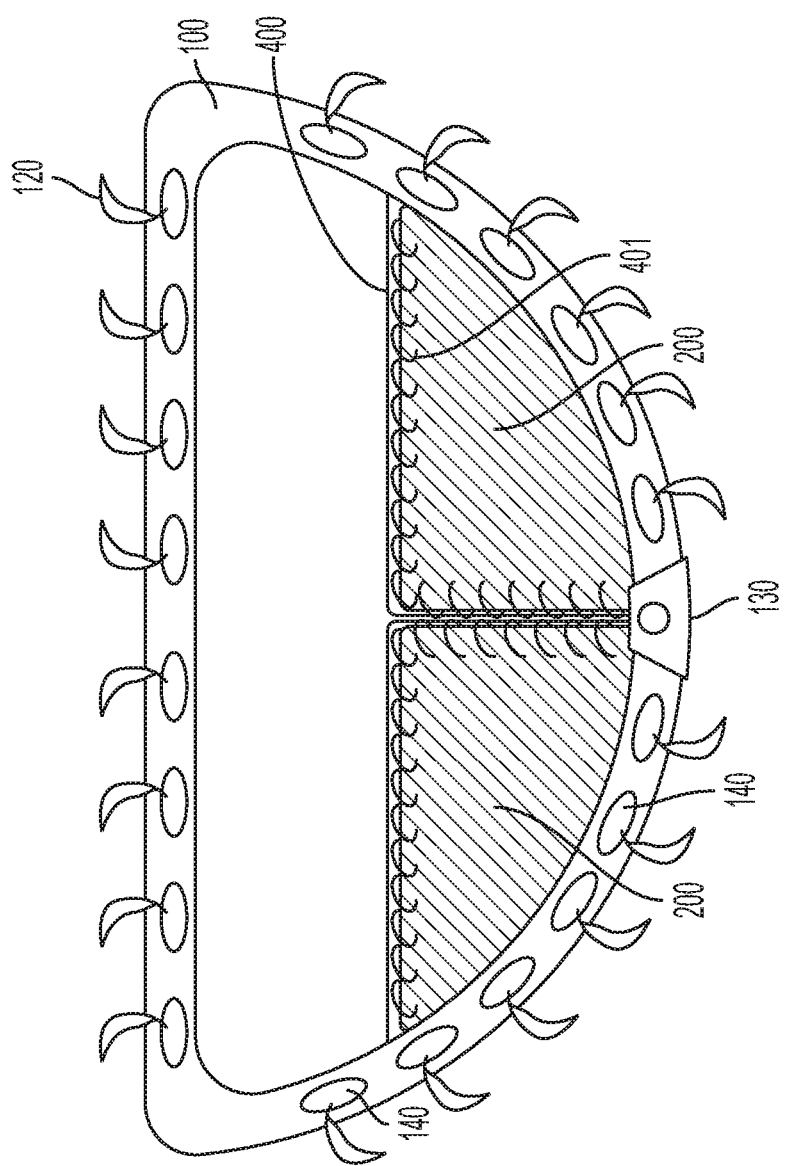
FIG. 1 depicts an annuloplasty ring having at least one synthetic leaflet in accordance with an embodiment.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by 1/10 of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the claims include equivalents to the recited values, e.g., variations in the numerical quantity of such values that can occur, but would be recognized to be equivalents by a person skilled in the art.

The term "patient" and "subject" are interchangeable and may be taken to mean any living organism. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human.

When implanting a replacement valve (e.g., an aortic valve, mitral valve, tricuspid valve, or other valve), the replacement valve can include a prosthesis attachment. The prosthesis can be configured to secure the replacement valve in a patient's heart. Additional detail related to prosthetic valves for mitral or tricuspid valve replacement can be found in: U.S. patent application Ser. No. 13/198,582 entitled "Percutaneous Transcatheter Repair of Heart Valves," filed Aug. 4, 2011; U.S. patent application Ser. No. 13/397,545 entitled "Percutaneous Transcatheter Repair of Heart Valves via Trans-Apical Access," filed Feb. 15, 2012; and U.S. patent application Ser. No. 13/779,478 entitled "Percutaneous Annuloplasty System with Anterior-Posterior Adjustment," filed Feb. 27, 2013, the contents of which are incorporated herein by reference in their entirety.

An implant and delivery system for introduction of a semi-rigid ring for treatment of tricuspid or mitral valve regurgitation includes an annuloplasty ring comprising an outer hollow member with a plurality of segments. In a further embodiment, segments may be adjustable and may cooperate with one another in order to change the outer hollow member from an elongated insertion shaped geometry to an annular operable shaped geometry. The tricuspid annuloplasty ring may include one or more zones comprising internal anchor members located at least partially within the outer hollow member. In one non-limiting embodiment, the tricuspid annuloplasty ring may include up to four different anchor zones, which are further discussed herein. In an embodiment, the internal anchor members may be configured to emerge sequentially from windows (i.e., openings) along the hollow tube, thereby engaging the tissue of the tricuspid valve annulus under treatment, potentially in a predetermined sequence.

Systems and methods are provided for introducing an annuloplasty ring (e.g., while it is housed in a linear shape within the delivery system) in a trans-apical or trans-femoral approach. In an embodiment, the distal tip of the delivery system may be introduced above the annulus. Once the annuloplasty ring is introduced, the plane of the annuloplasty ring may be rotated (e.g., automatically) to be parallel to the plane of the annulus. Once in the proper location, an embodiment may deploy a plurality of anchors. For example, an embodiment may deploy anchors associated with the septal zone, the posterior zone, or the first or second anterior zones.

The annuloplasty ring may then be snapped into a proper shape (e.g., a "D" shape) and introduced to the stabilization tool. The shape is possible because, as discussed herein, the annuloplasty ring comprises an outer hollow member with a plurality of segments, where the segments may be adjustable and may cooperate with one another in order to change the outer hollow member from an annular operable shaped geometry to an elongated insertion shaped geometry and vice versa.

Referring to FIG. 1, a top view of an annuloplasty ring 100, as it relates to various embodiments discussed herein, is shown. As shown, the annuloplasty ring 100 may have an annular operable shaped geometry where a first end and a second end are in mechanical communication through snap mechanism 130. In an embodiment, the annuloplasty ring may have an operable geometry. For example, the hypotube may be annular and/or D-shaped. Additionally, FIG. 1 illustrates a plurality of anchors 120 deployed through a plurality of anchor windows 140 of the annuloplasty ring 100. As shown in FIG. 1, the annuloplasty ring 100 may have at least one synthetic leaflet 200 in mechanical communication with the annuloplasty ring at a plurality of points on the inner surface of the annuloplasty ring 100. In some embodiments, the synthetic leaflet 200 may comprise a valve frame 400 having a proximal opening. The at least one synthetic leaflet may further comprise a synthetic leaflet material mechanically coupled to the valve frame, where the synthetic leaflet material is within the proximal opening. As depicted in FIG. 1, the at least one synthetic leaflet may comprise a plurality of leaflets, where the plurality of leaflets are mechanically coupled.

The annuloplasty ring may be made of various materials (e.g., a shape memory hypotube (nickel titanium (Ni—Ti) super elastic alloy)) cut to form a plurality of segments. Additionally, the cutting pattern used for laser processing (e.g. the cutting of anchor windows 140 through which anchors 120 may be deployed) of the annuloplasty ring 100 is illustrated in FIG. 1.

In an embodiment, the valve frame 400 may be made of various materials including, but not limited to, a shape memory metal (e.g. Ni—Ti). The valve frame 400 may have a diameter in a range of about 0.01 inches to about 0.015 inches. The synthetic leaflet material 200 may be mechanically coupled to the valve frame 400 by suturing (e.g. surgical sutures 401). This configuration may allow the at least one synthetic leaflet to move towards the surface of the annulus upon deployment of the annuloplasty ring. The suture material may be polytetrafluoroethylene (PTFE) or polypropylene sutures. Further embodiments may include a synthetic leaflet material made from a polymeric material (e.g. polyurethane or dried precordium tissue).

Figure 2:
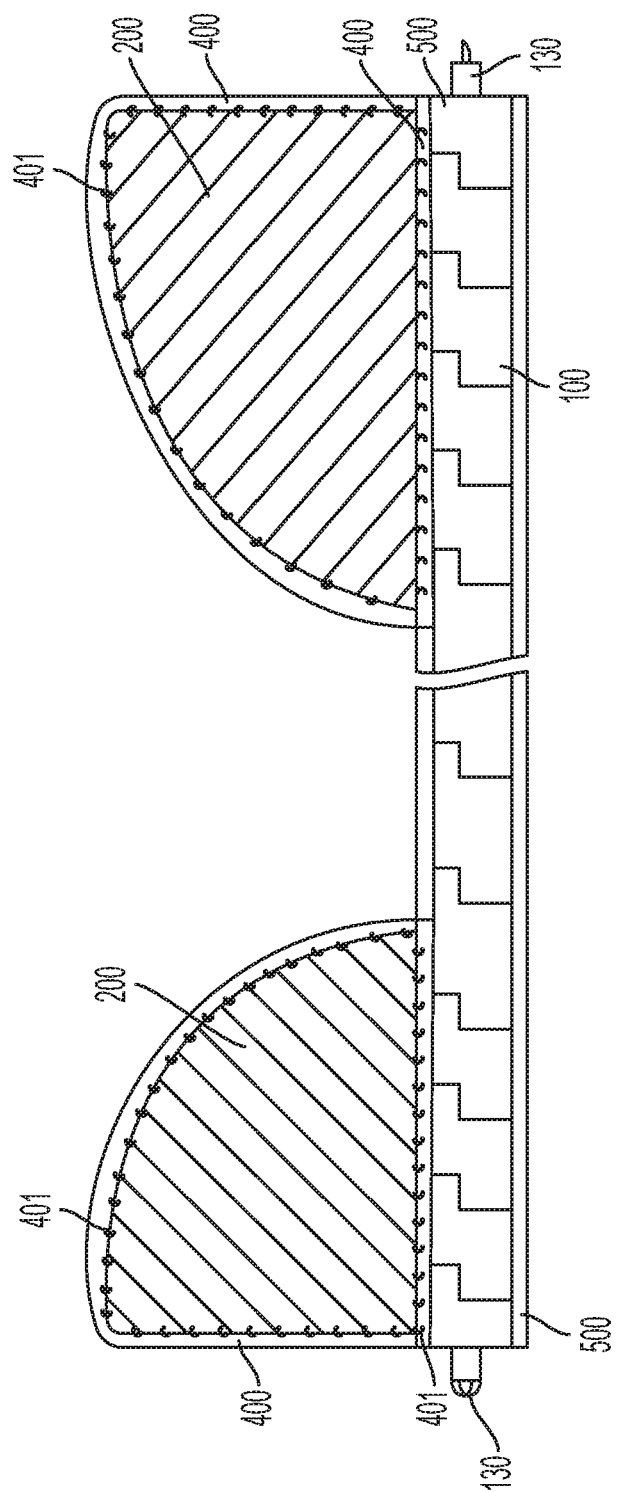
FIG. 2 illustrates an annuloplasty ring in an open configuration having at least one synthetic leaflet in accordance with an embodiment.

Referring to FIG. 2, a top view of the annuloplasty ring 100, as it relates to various embodiments discussed herein, is shown. As shown, the annuloplasty ring 100 may have an elongate insertion geometry where the first end is opposite the second end. In some embodiments, the first end, the second end, or both may have a snap mechanism 130. In some embodiments, the annuloplasty ring 100 may have a coating 500 (e.g. a DACRON coating) on the inner surface or the outer surface of the annuloplasty ring 100. In further embodiments, the annuloplasty ring 100 may have at least one synthetic leaflet 200. As depicted in FIG. 2, the at least one synthetic leaflet may comprise a plurality of leaflets positioned at the first end or the second end of the annuloplasty ring.

Figure 3:
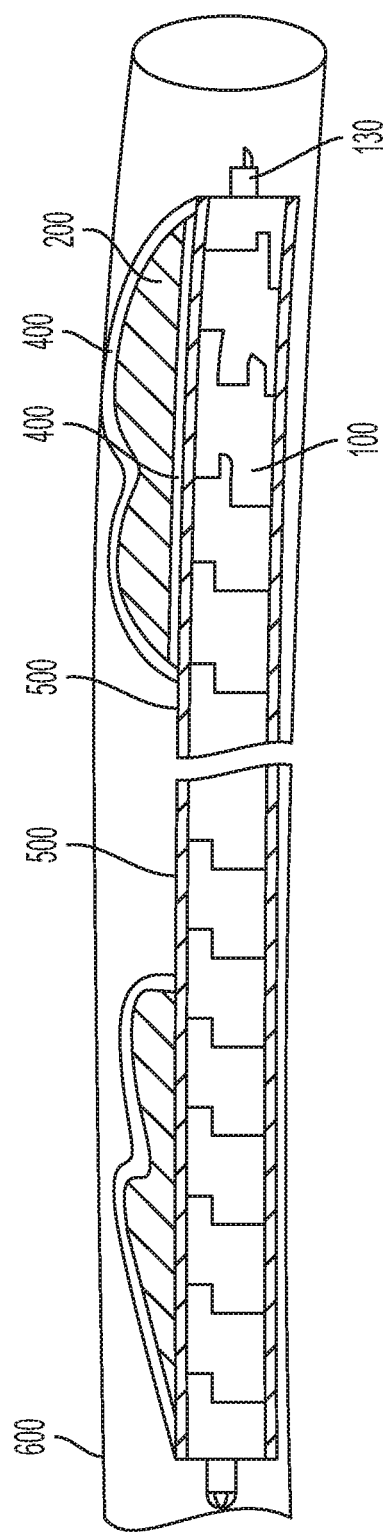
FIG. 3 depicts a cross-sectional view of an annuloplasty ring in an elongate insertion geometry in accordance with an embodiment.

Illustrated in FIG. 3 is a cross section view of an annuloplasty ring in an elongate insertion geometry within a delivery catheter 600.

Figure 4:
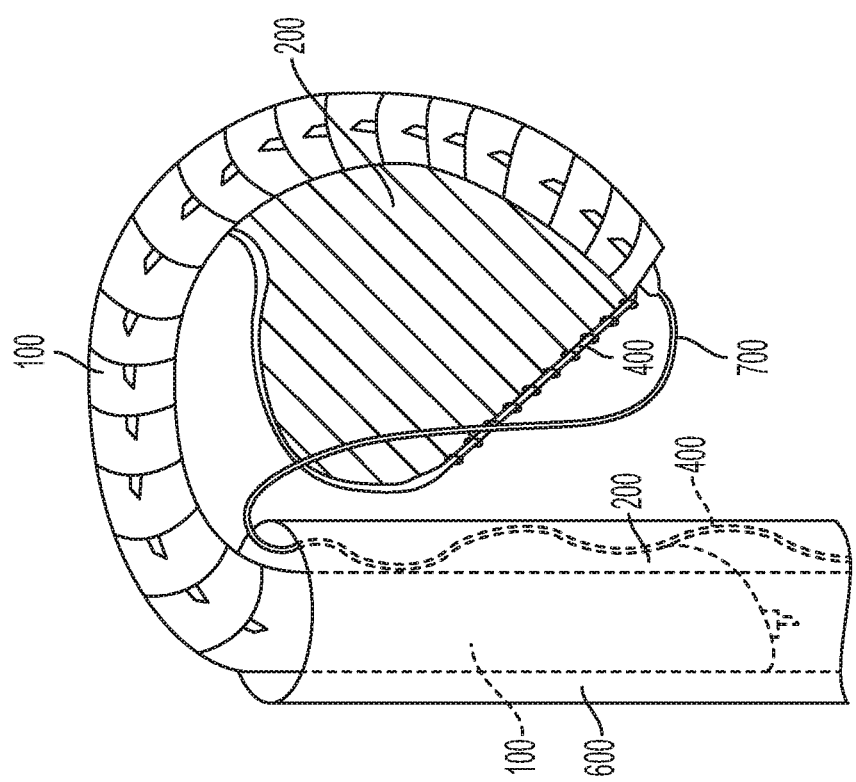
FIG. 4 illustrates a perspective view of an annuloplasty ring having at least one synthetic leaflet in accordance with an embodiment.

FIG. 4 illustrates a side view of a distal end of the delivery catheter 600 with the annuloplasty ring 100 and the at least one synthetic leaflet 200 partially deployed from the distal end of the delivery catheter. Further illustrated in FIG. 4 is a pull-wire 700 that can be in mechanical communication with the annuloplasty ring 100.

Figure 5A:
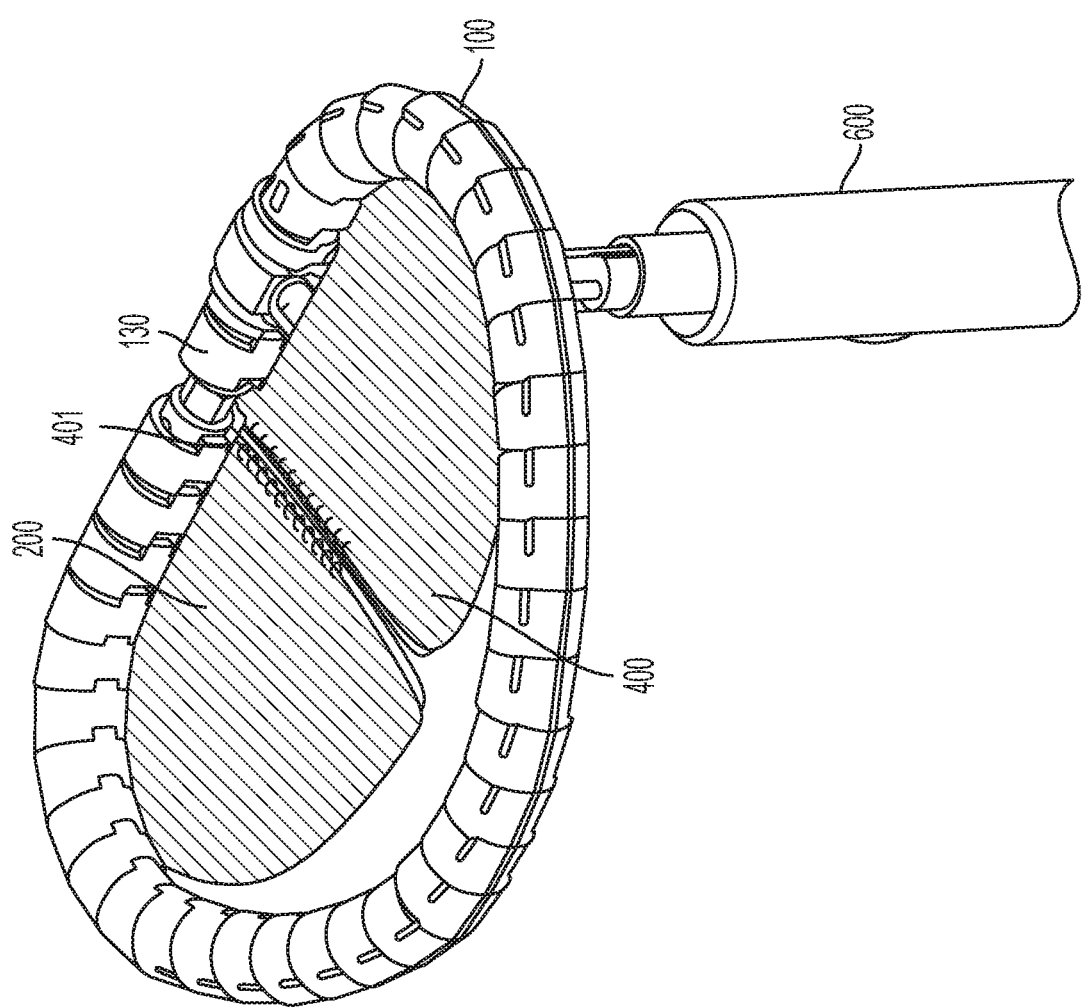
FIG. 5A is a perspective view depicting delivery of an annuloplasty ring having at least one synthetic leaflet in accordance with an embodiment.
Figure 5B:
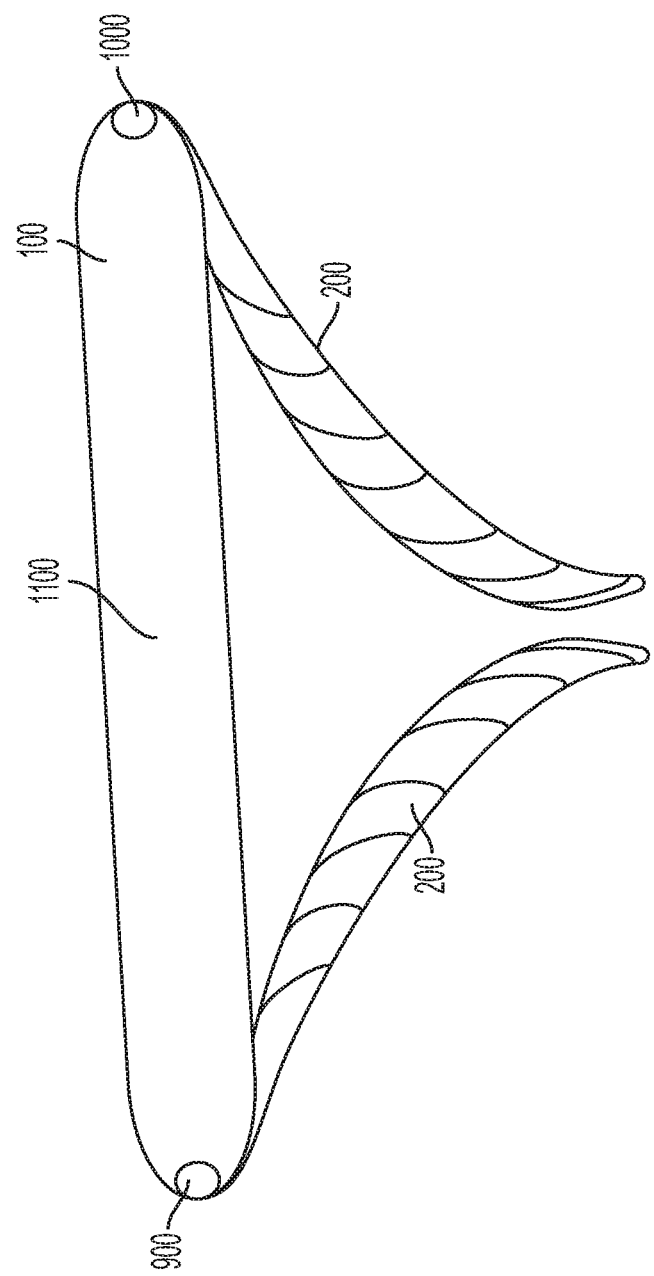
FIG. 5B illustrates a side view of an annuloplasty ring having at least one synthetic leaflet in accordance with an embodiment.
Figure 5C:
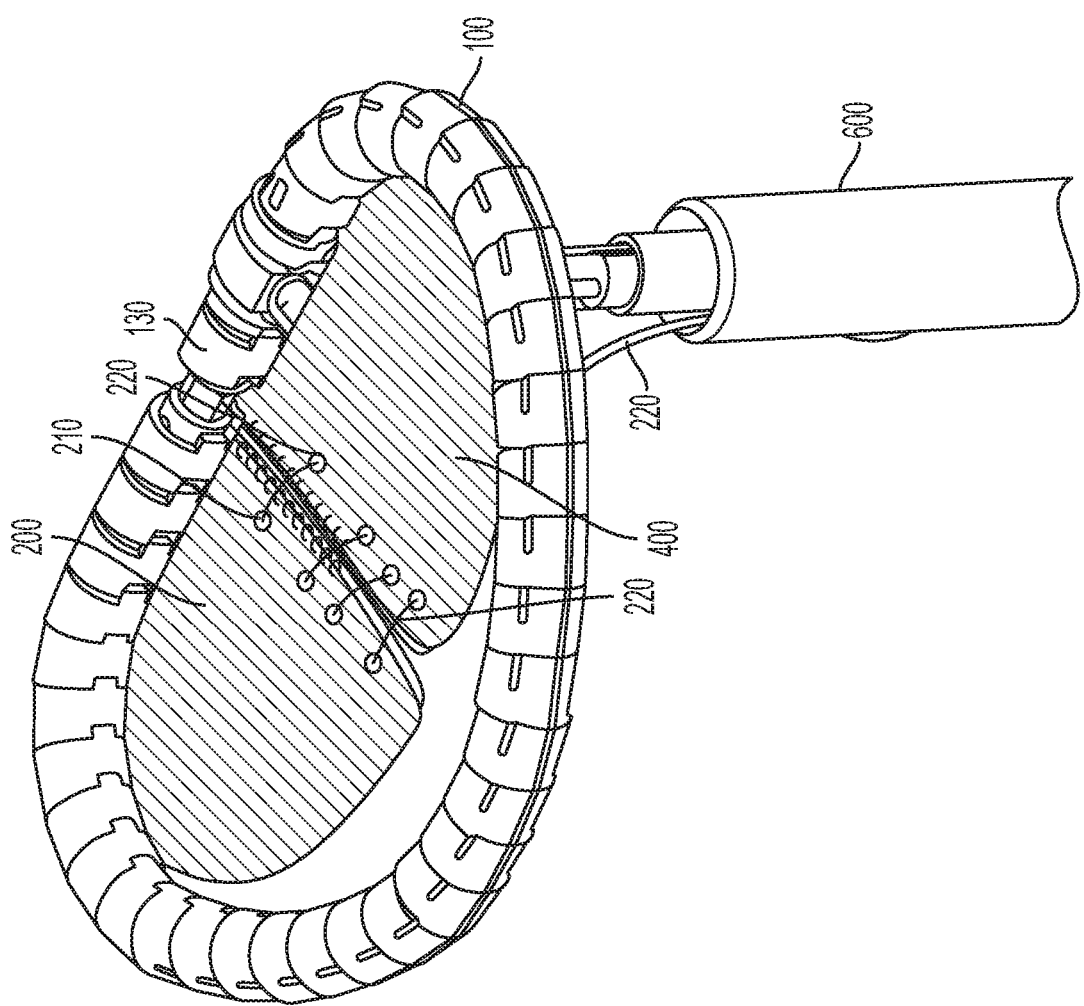
FIG. 5C is a perspective view depicting delivery of an annuloplasty ring having at least one synthetic leaflet in accordance with an embodiment.

FIGS. 5A-C depict perspective views of the annuloplasty ring 100 where the plane of the annuloplasty ring 100 (in its annular operable geometry) has been changed to be perpendicular to the longitudinal axis of the delivery catheter 600. As illustrated in FIG. 5A, the at least one synthetic leaflet 200 comprises a plurality of leaflets in mechanical communication. In some embodiments, the plurality of leaflets in mechanical communication are configured to be operably connected to the inner surface of the posterior side 900 of the annuloplasty ring 100. In further embodiments, the plurality of leaflets in mechanical communication are configured to be operably connected to the inner surface of the anterior side 1000 of the annuloplasty ring 100. As illustrated in FIG. 5B, in some embodiments annuloplasty ring 100 may comprise ring element 1100.

FIG. 5C depicts a further embodiment wherein annuloplasty ring 100 comprises a plurality of leaflets having one or more lace holes 210. The plurality of leaflets may be configured to be in mechanical communication using a suture lace 220 that operably connects the plurality of leaflets through the one or more lace holes 210. In further embodiments, the suture lace 220 can be configured to pass through the snap mechanism 130 and into the delivery catheter 600.

Figure 6:
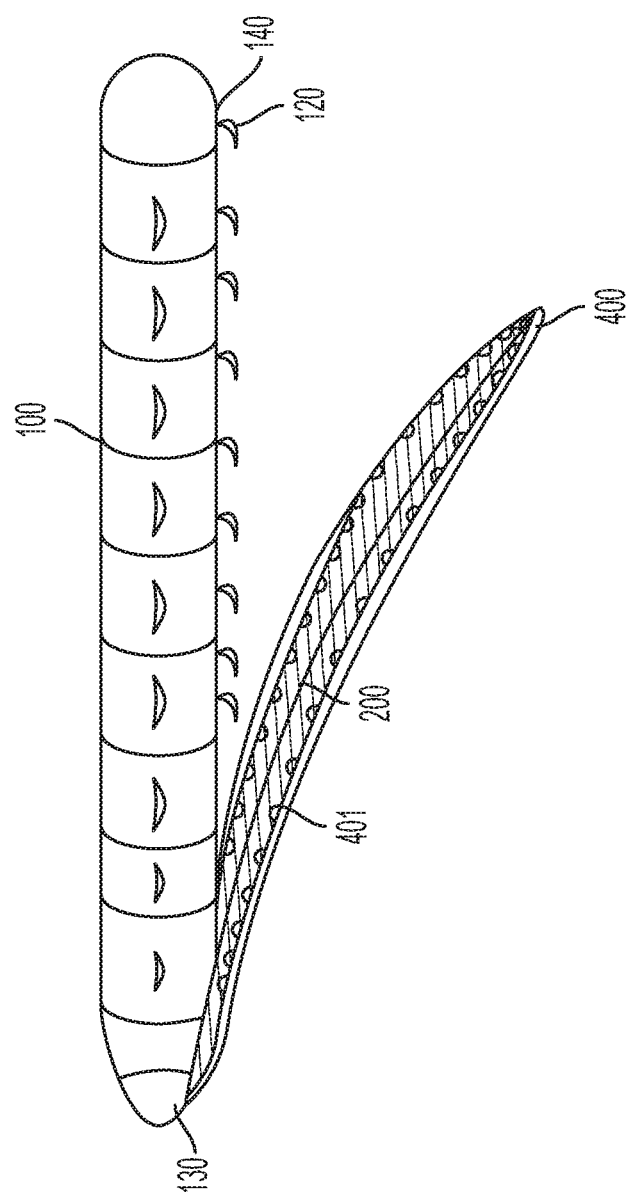
FIG. 6 is a perspective view of an annuloplasty ring having at least one synthetic leaflet in an open configuration in accordance with an embodiment.

FIG. 6 depicts the deployed annuloplasty ring 100 and the deployed plurality of anchors 120 with at least one synthetic leaflet 200 tilted toward the annulus and a native posterior leaflet.

Figure 7:
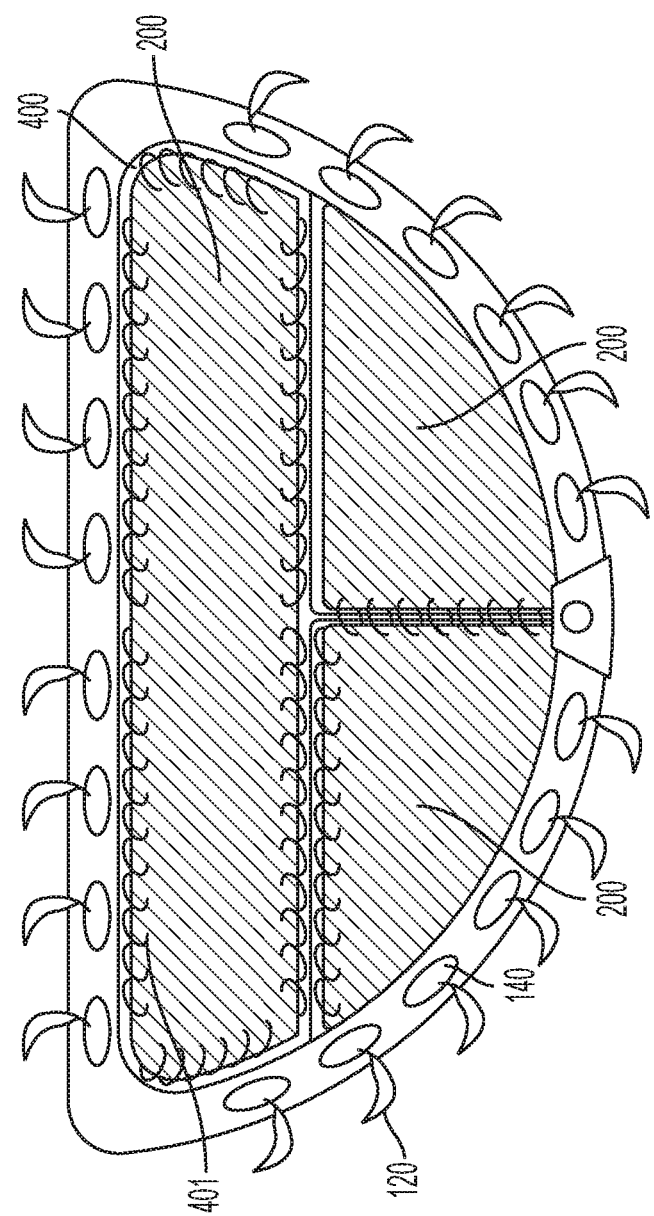
FIG. 7 depicts an annuloplasty ring having at least one anterior synthetic leaflet and at least one posterior synthetic leaflet in accordance with an embodiment.
Figure 8:
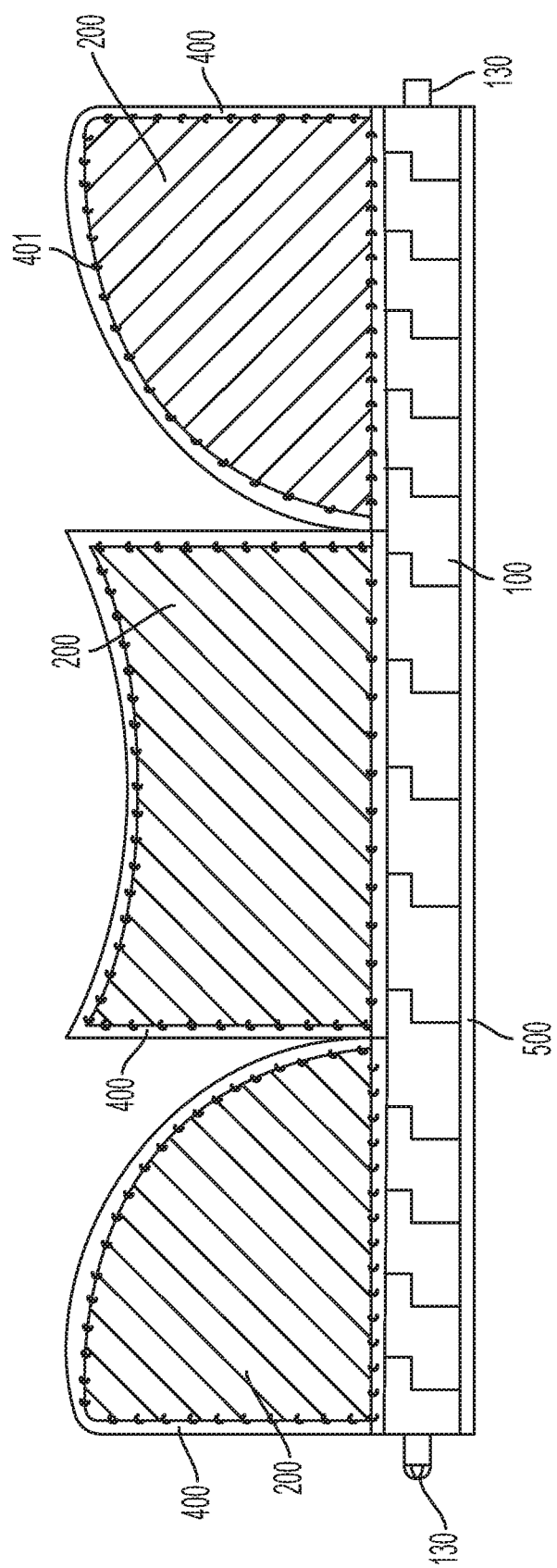
FIG. 8 is a cross-section view of an annuloplasty ring having at least one anterior synthetic leaflet and at least one posterior synthetic leaflet in accordance with an embodiment.

Referring to FIGS. 7-8, the annuloplasty ring 100, as it relates to various embodiments discussed herein, is shown. As shown, the annuloplasty ring 100 in an annular operable geometry (FIG. 7) or an elongate insertion geometry (FIG. 8) may comprise a plurality of leaflets 200. In some embodiments, the inner surface of the posterior side of the annuloplasty ring 100 may comprise a plurality of leaflets having lace holes that provides mechanical communication for the plurality of leaflets. The plurality of leaflets may be in mechanical communication with the inner surface of the posterior side of the annuloplasty ring 100 at a plurality of points.

Figure 12:
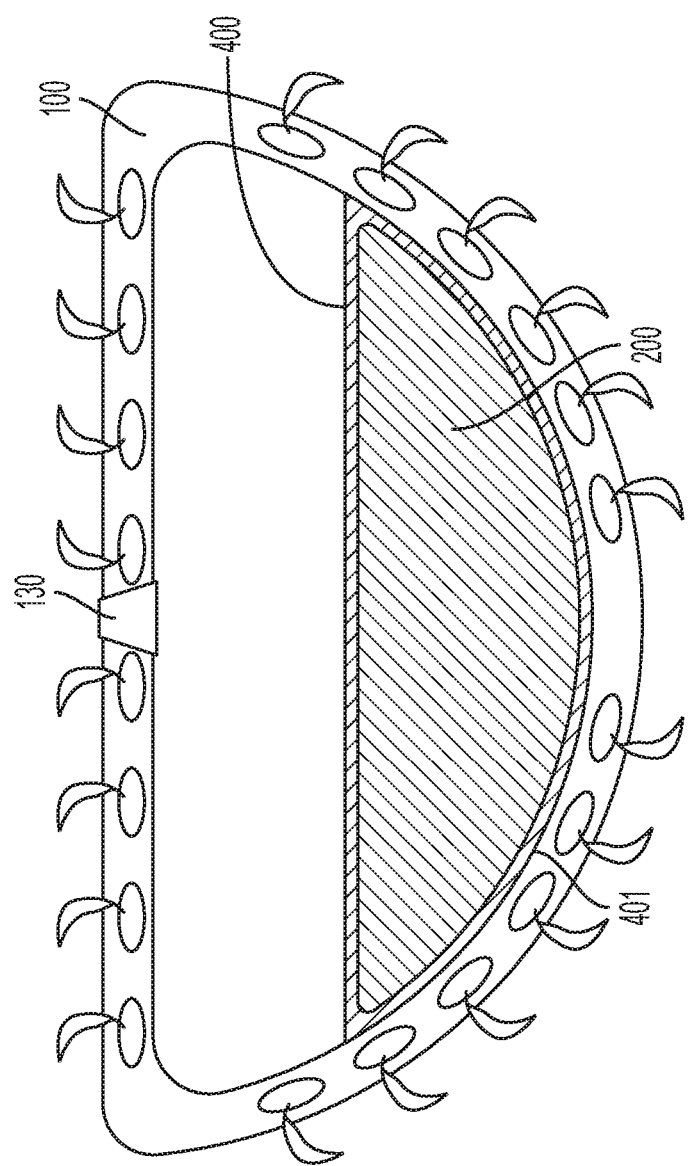
FIG. 12 is a top view of an annuloplasty ring having at least one posterior synthetic leaflet in accordance with an embodiment.

In a further embodiment, as illustrated in FIG. 12, the annuloplasty ring may comprise at least one synthetic leaflet on the inner surface of the posterior side of the annuloplasty ring 100. The at least one synthetic leaflet may be in mechanical communication with the inner surface of the posterior side of the annuloplasty ring 100 at a plurality of points. Further, the snap mechanism 130 can be located on the anterior side of the annuloplasty ring 100.

Figure 13:
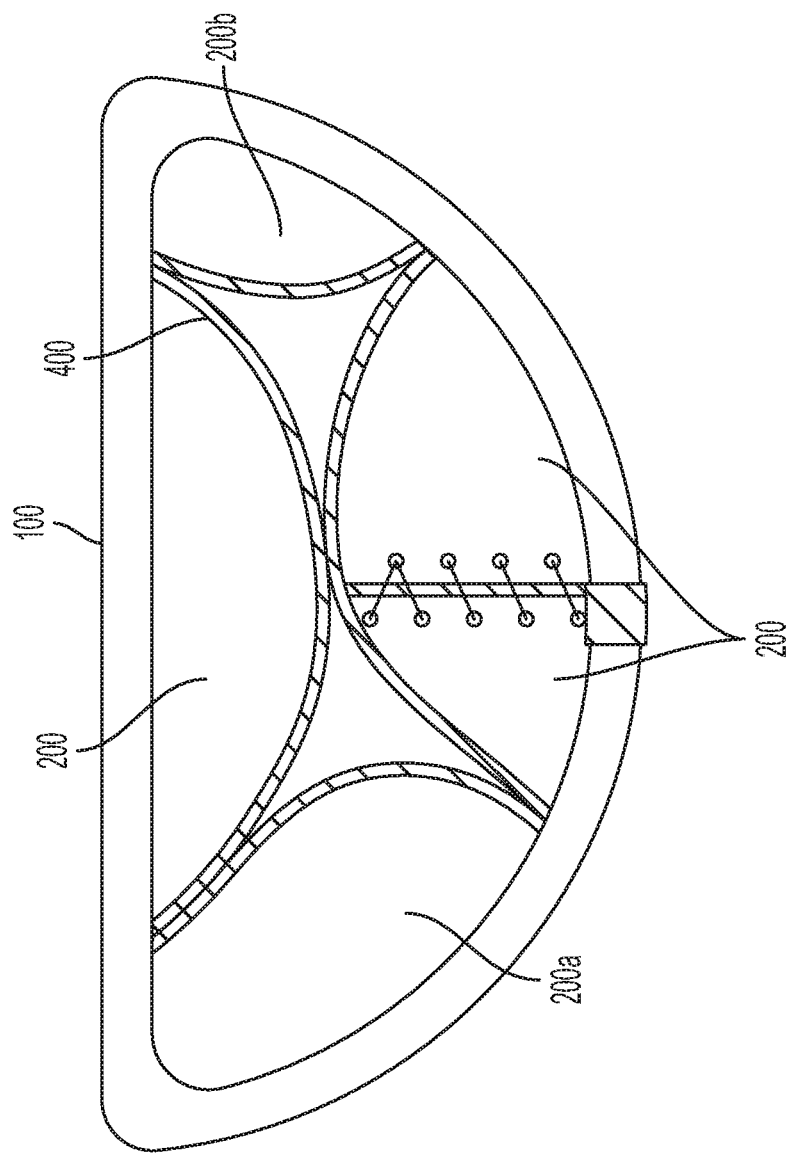
FIG. 13 depicts an annuloplasty ring having a plurality of synthetic leaflets in accordance with an embodiment.

In a further embodiment, as illustrated in FIG. 13, the inner surface of the posterior side of the annuloplasty ring 100 may comprise a plurality of leaflets having lace holes that provide mechanical communication for the plurality of leaflets. The plurality of leaflets may be in mechanical communication with the inner surface of the posterior side of the annuloplasty ring 100 at a plurality of points. Further, the inner surface of the anterior side of the annuloplasty ring 100 may comprise at least one synthetic leaflet 200 in mechanical communication with the inner surface of the annuloplasty ring 100. In some embodiments, as depicted in FIG. 13, the inner surface of the annuloplasty ring 100 may comprise a plurality of commissure leaflets 200*a,b*.

Figure 9:
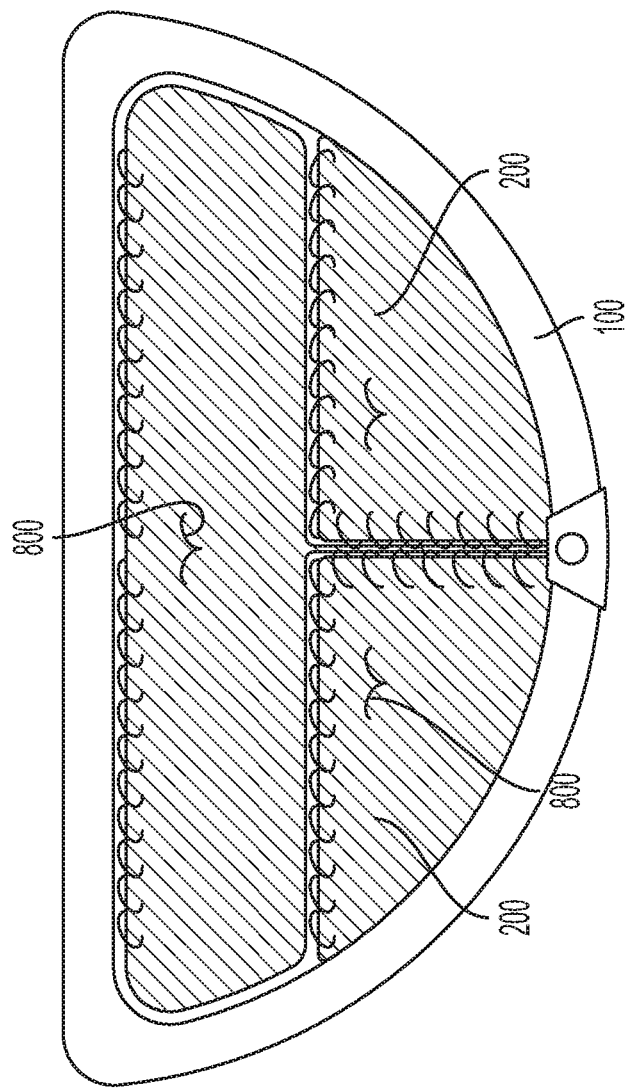
FIG. 9 is a top view of an annuloplasty ring having at least one anterior synthetic leaflet and at least one posterior synthetic leaflet secured to a native leaflet with a leaflet anchor in accordance with an embodiment.
Figure 10:
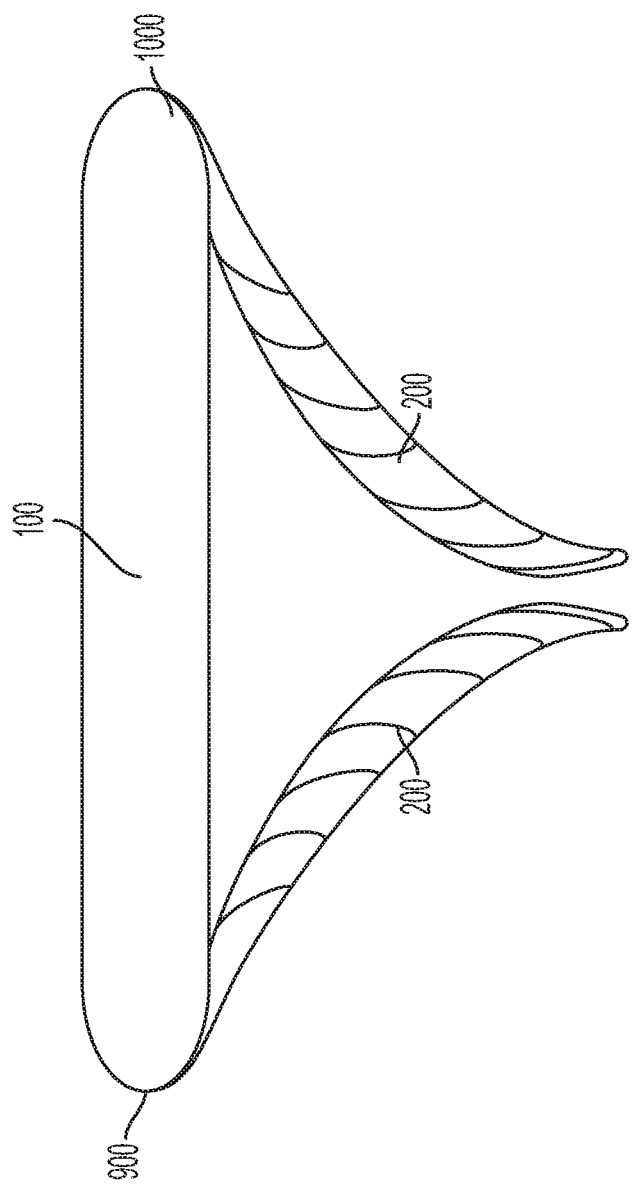
FIG. 10 is a side view of an annuloplasty ring having at least one synthetic leaflet in accordance with an embodiment.

In some embodiments, as illustrated in FIG. 9, a leaflet anchor 800 may be in mechanical communication with the at least one synthetic leaflet 200 of the annuloplasty ring 100. In some embodiments, the leaflet anchor 800 may mechanically couple one or more native leaflets to the at least one synthetic leaflet 200. This embodiment may allow the one or more synthetic leaflets 200 to co-apt, as illustrated in FIG. 10.

Figure 11A:
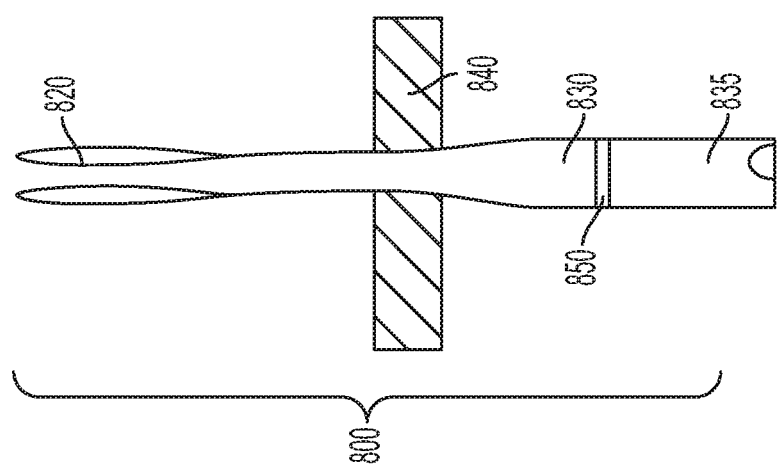
FIG. 11A illustrates a leaflet anchor in accordance with an embodiment.
Figure 11C:
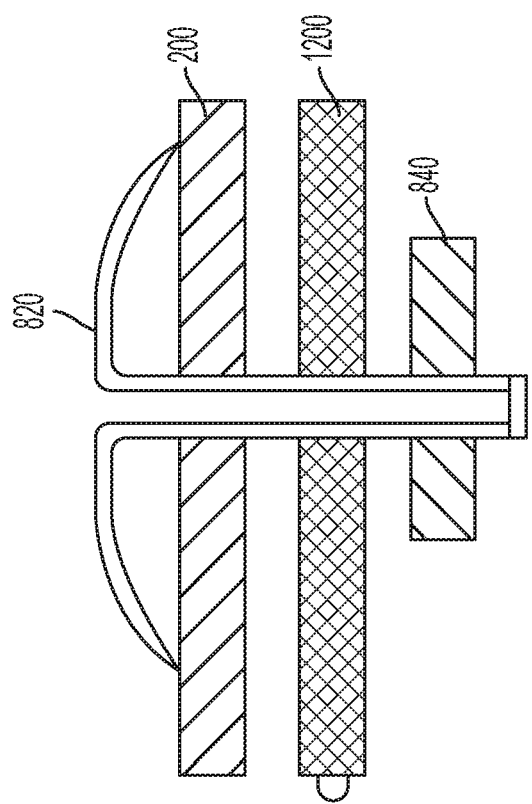
FIG. 11C illustrates a deployed leaflet anchor in accordance with a further embodiment.

As illustrated in FIG. 11A-C, the leaflet anchor 800 may have an anchor body 830 with a first end and a second end. The leaflet anchor 800 may further comprise an anchor portion 820 in mechanical communication with the first end of the leaflet anchor. In further embodiments, the leaflet anchor 800 may also include a separating element 850 in mechanical communication with the second end of leaflet anchor. Separating element 850 can be configured to separate the anchor delivery catheter 835 and the leaflet anchor 800. The leaflet anchor 800 may also comprise a disk portion 840, where the disk portion is in mechanical communication with the anchor body 830 between the first end and the second end. As illustrated in FIG. 11B, leaflet anchor 800 can be configured to deploy from delivery catheter 600, from anchor delivery catheter 835, or a combination thereof. In some embodiments, leaflet anchor 800 may be configured to pass through native leaflet 1200 and the at least one synthetic leaflet 200, wherein anchor portion 820 is deployed on a surface of the at least one synthetic leaflet 200. In some embodiments, the disk portion 840 can be configured to fix the anchor portion 820 to the at least one synthetic leaflet 200 and the native leaflet 1200.

The annuloplasty ring as described above can be designed and shaped for various functions such as mitral valve replacement. A similar annuloplasty ring can be designed and constructed for tricuspid valve replacement as well. However, a tricuspid ring can be designed with additional features, such as a release zone positioned on the ring assembly at a location that will be adjacent to a patient's atrioventricular node or valves. In certain implementations, the release zone does not have any anchors. Rather, the alternate shape and profile of the release zone provides for interference between the annuloplasty ring and the patient's atrioventricular node or valves, thereby securing the ring assembly in position.

Some embodiments are directed towards a method of delivering the annuloplasty ring as substantially described above. In some embodiments, the annuloplasty ring may be delivered in an elongate insertion geometry, where the delivery of the annuloplasty ring utilizes one of a trans-apical approach, trans-septal approach, trans-femoral approach, trans-jugular approach, or a trans-atrial approach.

This disclosure is not limited to the particular apparatus, systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In the detailed description above, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different devices or applications. Various presently unforeseen or unanticipated alternatives, modifications, variations or improvements therein may be subsequently made by those skilled in the art, each of which is also intended to be encompassed by the disclosed embodiments.

What is claimed is:

1. An annuloplasty device comprising:
    an annuloplasty ring comprising a first end and a second end opposite the first end, the annuloplasty ring configured to transition between an elongate insertion geometry and an annular operable geometry;
    a plurality of anchors disposed within the annuloplasty ring, the plurality of anchors configured to assume a deployment configuration when the annuloplasty ring is in the annular operable geometry; and
    a plurality of leaflets in mechanical communication with and mechanically coupled directly to the annuloplasty ring at a plurality of points, at least one leaflet of the plurality of leaflets comprising (i) a valve frame comprising a proximal opening, and (ii) a synthetic leaflet material mechanically coupled to the valve frame, the synthetic leaflet material disposed within the proximal opening,
    wherein the plurality of leaflets comprises a first leaflet positioned adjacent to the first end of the annuloplasty ring and a second leaflet positioned adjacent to the second end of the annuloplasty ring.

2. The annuloplasty device of claim 1, wherein the valve frame comprises a shape memory metal.

3. The annuloplasty device of claim 1, wherein the synthetic leaflet material comprises a polymeric material.

4. An annuloplasty device comprising:
    an annuloplasty ring comprising a first end and a second end opposite the first end, the annuloplasty ring configured to transition between an elongate insertion geometry and an annular operable geometry;
    a plurality of anchors disposed within the annuloplasty ring, the plurality of anchors configured to assume a deployment configuration when the annuloplasty ring is in the annular operable geometry; and
    a plurality of leaflets in mechanical communication with and mechanically coupled directly to the annuloplasty ring at a plurality of points,
    wherein the plurality of leaflets comprises a first leaflet positioned adjacent to the first end of the annuloplasty ring and a second leaflet positioned adjacent to the second end of the annuloplasty ring, at least a portion of each of the first leaflet and the second leaflet mechanically coupled to one another.

5. The annuloplasty device of claim 4, wherein the plurality of points are on a posterior side of a native valve.

6. The annuloplasty device of claim 4, wherein at least one leaflet of the plurality of leaflets is in mechanical communication with the annuloplasty ring at a subset of points of the plurality of points on an anterior side of the native valve.

7. The annuloplasty device of claim 4, wherein the annuloplasty ring further comprises a plurality of anchor windows through which the plurality of anchors are deployable.

8. The annuloplasty device of claim 4, wherein the annuloplasty ring comprises a coating.

9. The annuloplasty device of claim 8, wherein the coating comprises a polyethylene terephthalate coating.

10. The annuloplasty device of claim 4, wherein the annuloplasty ring comprises a shape memory metal.

11. The annuloplasty device of claim 4, wherein the annuloplasty ring further comprises at least one snap mechanism configured to connect the first end and the second end.

12. The annuloplasty device of claim 4, wherein at least one leaflet of the plurality of leaflets comprises a synthetic leaflet material.

13. An annuloplasty device comprising:
    an annuloplasty ring comprising a first end and a second end opposite the first end, the annuloplasty ring configured to transition between an elongate insertion geometry and an annular operable geometry;
    a plurality of anchors disposed within the annuloplasty ring, the plurality of anchors configured to assume a deployment configuration when the annuloplasty ring is in the annular operable geometry; and
    a plurality of leaflets in mechanical communication with and mechanically coupled directly to the annuloplasty ring at a plurality of points, at least one leaflet of the plurality of leaflets comprising one or more lace holes configured to receive a suture therethrough,
    wherein the plurality of leaflets comprises a first leaflet positioned adjacent to the first end of the annuloplasty ring and a second leaflet positioned adjacent to the second end of the annuloplasty ring.

14. A method of implanting an annuloplasty device within a patient, the method comprising:
    delivering, into the patient, an annuloplasty ring in an elongate insertion geometry, the annuloplasty ring comprising a plurality of leaflets in mechanical communication with and mechanically coupled directly to the annuloplasty ring at a plurality of points; and positioning the annuloplasty ring parallel to a plane of a valve annulus of the patient, wherein the plurality of leaflets comprise a first leaflet positioned adjacent to the first end of the annuloplasty ring and a second leaflet positioned adjacent to the second end of the annuloplasty ring, at least a portion of each of the first leaflet and the second leaflet mechanically coupled to one another.

15. The method of claim 14, wherein the annuloplasty ring is delivered using one of a trans-apical approach, a trans-septal approach, a trans-femoral approach, a trans-jugular approach, or a trans-atrial approach.

16. The method of claim 14, wherein at least one leaflet of the plurality of leaflets comprises:

a valve frame comprising a proximal opening; and a synthetic leaflet material mechanically coupled to the valve frame, wherein the synthetic leaflet material is disposed within the proximal opening.

17. The method of claim 16, wherein the valve frame comprises a shape memory metal.

18. The method of claim 16, wherein the synthetic leaflet material comprises a polymeric material.

19. The method of claim 14, wherein at least one leaflet of the plurality of leaflets comprises a synthetic leaflet material.

* * * * *